(12) United States Patent
Madhavamenon et al.

(10) Patent No.: US 11,007,243 B2
(45) Date of Patent: May 18, 2021

(54) ENZYME-ASSISTED SUPERCRITICAL EXTRACTION OF NIGELLA SATIVA SEEDS

(71) Applicant: AKAY FLAVOURS & AROMATICS PVT, LTD, Kerala (IN)

(72) Inventors: Krishnakumar Illathu Madhavamenon, Ernakulam (IN); Balu Paulose Maliakel, Ernakulam (IN); Sibi Perumbamkudiyil Ittiyavirah, Rimsr (IN); Kannan Ramalingam, Kottayam (IN)

(73) Assignee: AKAY FLAVOURS & AROMATICS PVT, LTD, Kerala (IN)

( * ) Notice: Subject to any disclaimer, the term of this patent is extended or adjusted under 35 U.S.C. 154(b) by 0 days.

(21) Appl. No.: 16/663,714

(22) Filed: Oct. 25, 2019

(65) Prior Publication Data

US 2020/0054704 A1    Feb. 20, 2020

Related U.S. Application Data

(62) Division of application No. 15/805,450, filed on Nov. 7, 2017, now Pat. No. 10,485,837.

(30) Foreign Application Priority Data

Nov. 7, 2016   (IN) ............................. 201641037970

(51) Int. Cl.
| | | |
|---|---|---|
| *A61K 36/00* | (2006.01) | |
| *A61K 36/71* | (2006.01) | |
| *A61K 31/122* | (2006.01) | |
| *A61K 31/202* | (2006.01) | |
| *A61K 31/192* | (2006.01) | |

(52) U.S. Cl.
CPC ............ *A61K 36/71* (2013.01); *A61K 31/122* (2013.01); *A61K 31/192* (2013.01); *A61K 31/202* (2013.01); *A61K 2236/19* (2013.01); *A61K 2236/333* (2013.01); *A61K 2236/37* (2013.01)

(58) Field of Classification Search
None
See application file for complete search history.

(56) References Cited

U.S. PATENT DOCUMENTS

| 6,218,434 | B1 | 4/2001 | Crooks et al. |
|---|---|---|---|
| 8,501,250 | B2 | 8/2013 | Ismail et al. |
| 2002/0132019 | A1 | 9/2002 | Kandil |
| 2003/0060454 | A1 | 3/2003 | Kandil |
| 2003/0060508 | A1 | 3/2003 | Kandil |
| 2005/0214241 | A1 | 9/2005 | Kandil |
| 2008/0152736 | A1 | 6/2008 | Kandil |
| 2011/0076346 | A1 | 3/2011 | Babish et al. |
| 2012/0046366 | A1* | 2/2012 | Ismail ...................... A61P 9/12  514/675 |
| 2012/0244234 | A1 | 9/2012 | Etheve et al. |

FOREIGN PATENT DOCUMENTS

| WO | WO 2010/050794 A1 | 5/2010 |
|---|---|---|
| WO | WO 2010/133574 A1 | 11/2010 |
| WO | WO 2015/086239 A1 | 6/2015 |

OTHER PUBLICATIONS

Ahmad A., *Asica Pac J Trop Biomed.* 3(5):337-352 (2013).
Al-Ali, et al., *J. Ayub. Med. Coll. Abbottabad* 20:25-27 (2008).
Barkus, et al., *European Journal of Pharmacology* 626:49-56 (2010).
Becker, et al., *Psychopharmacology* 144:333-338 (1999).
Beuzen, et al., *Physiology and behavior* 58(1):111-118 (1995).
Blokland, A., *Brain Research Reviews* 21(3):285-300 (1995).
Corbett, et al., *Neuropharmacology* 32(5):461-466 (1993).
Didi, et al., Metabolic and Antioxidant Effects of Nigella Sativa Oil on Prevention of Obesity Development in Rats Fed High-Fat Diet. *European Chemical Bulletin* (2014), vol. 3, No. 9, pp. 888-896 (Year: 2014).
Dong, et al., *Occupational Medicine* 67:534-539 (2017).
Dunn, et al., *European Journal of Pharmacology* 169:1-10 (1989).
Gharby, et al., *J Saudi Society of Agricultural Sciences* 14(2):172-177 (2015).
Groot, et al., *FEBS Letters* 400(3):309-314 (1997).
Kalueff, *Neural Plasticity*, retrieved from https://doi.org/10.1155/2007/78171 (2007).
Kulkarni, et al., *Indian Journal of Pharmacology* 42(3):168-173 (2010).
Leijdekkers, M.L., et al., *Headache* 30:352-358 (1990).
Lieb, et al., *Journal of Neurochemistry* 93(3):549-559 (2005).
Niemi, P.M., et al., *Acta Psychiatr Scand.* 106:461-463 (2002).
O'Shea, et al., *Journal of Pscychopharmcology* 18(4):502-508 (2004).
Prashar, et al., *Pharmacology and Pharmacy* 4:65-76 (2014).
Randhawa, J., *Ayub. Med. Coll. Abbottabad.* 20:1-2 (2008).
Roghani, et al., *Pejouhandeh.* 17(5):219-227 (2012).
Roth, et al., *J. Clinical Pharmacol.* 18(1S):45S-49S (1984).
Salim, et al., *Molecules* 18(9):11219-11240 (2013).
Sinclair, et al., *Eval Health Prof.* 35(3):259-279 (2012).
Spira, et al., *J Gerontol A Biol Sci Med Sci.* 67A(4):433-439 (2012).
Staples, et al., *NPJ Schizophr.* 37:1-6 (2017).
Wiley, et al., *European Journal of Pharmacology* 294:101-107 (1995).

\* cited by examiner

*Primary Examiner* — Qiuwen Mi
(74) *Attorney, Agent, or Firm* — Brinks Gilson & Lione

(57) ABSTRACT

The present invention relates to novel black cumin extract compositions and a green process for making the composition. The black cumin extract composition of the invention can be used to treat anxiety, sleep and stress disorders along with significant effect on memory enhancement. The composition is available in oil and powder forms.

6 Claims, 9 Drawing Sheets

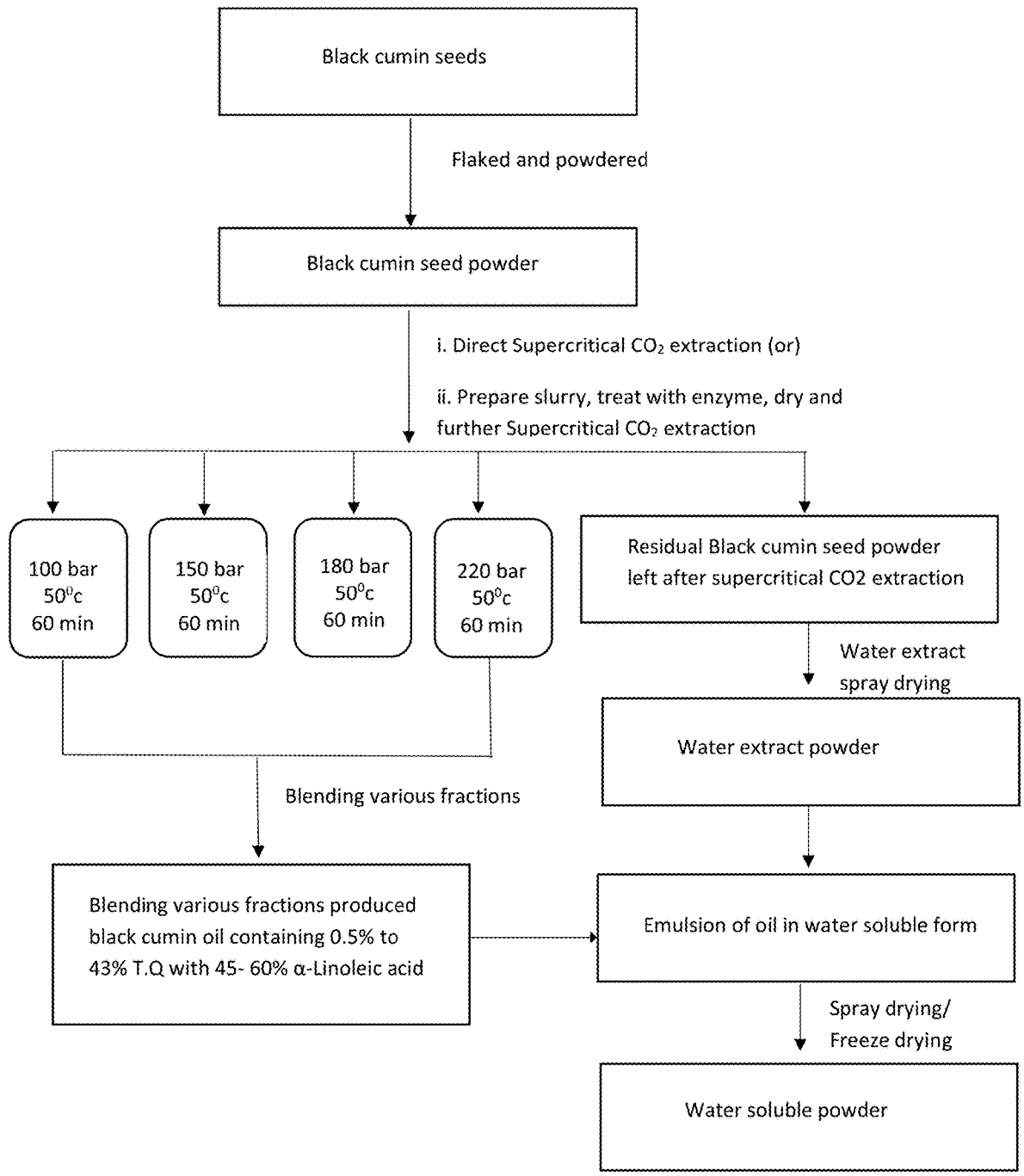

ENZYME-ASSISTED SUPERCRITICAL EXTRACTION OF NIGELLA SATIVA SEEDS

REFERENCE TO EARLIER FILED APPLICATION

This application is a divisional application of U.S. application Ser. No. 15/805,450, filed Nov. 7, 2017, which claims the benefit of the filing date of Indian Provisional Patent Application No. IN201641037970, filed Nov. 7, 2016, the disclosure of which is incorporated, in its entirety, by this reference.

FIELD OF THE INVENTION

The present invention relates to the field of health protective nutraceutical compositions, more particularly to a green process for preparing black cumin seed extract composition having significant therapeutic properties to treat anxiety, stress and sleep disorders along with significant memory enhancement at relatively lower dosage.

BACKGROUND OF THE INVENTION

Anxiety corresponds to an emotional and unpleasant state of nature associated with tension, stress, apprehension or uneasiness, discomfort and concern or fear about some defined or undefined future threat. Anxiety is commonly characterized by psychological symptoms like lack of concentration, sympathetic and somatic symptoms including tachycardia, tremors, sweating, gastrointestinal tract (GIT) disturbances, etc. Fatigue and sleep disturbances were also found to be common signs of anxiety. Some degree of anxiety is a part of normal life, but if anxiety conditions persist it impairs a person's ability to perform a job and often leads to visceral organ dysfunction and neurological problems.

In anxiety conditions the stress hormone cortisol is being released in large amounts which affects the brain and leads to memory loss and may cause problems related to memory recall. Sleep deprivation which occurs during anxiety also affects a person's memory and even may lead to dementia.

It has been observed that anxiety and memory are two closely related paradigms. Anatomically, brain structures such as hippocampus/amygdala are implicated both in anxiety and memory (Beuzen and Belzung C, *Physiology and behavior* 58(1); 1995: 111-118.) Anxiety, depression and calming effect are interrelated functions in the brain. For example, administration of THC (Tetrahydrocannabinol) in animals impaired the memory and simultaneously found to increase the symptoms of anxiety. Similar type of effect was found to occur in humans during acute administration of cannabinoids. (O'Shea et al *Journal of Pscychopharmcology* 18 (4); 2004: 502-508). There are reports that various monoamines (catecholamines) can interfere with memory enhancement and anxiety. Increase in brain serotonergic transmission can interfere with memory and learning acquisition (Niemi P M et al., *Acta Psychiatr Scand.* 2002; 106: 461-63). The role of 5-HT in anxiety is very clearly established. Increase in brain 5-HT levels leads to anxiety while decrease in brain 5-HT levels leads to anti-anxiety. (Leijdekkers M L et al., *Headache.* 1990; 30: 352-58).

The symptoms or conditions of severe anxiety should be treated with anxiolytics. Some drugs functions both as anxiolytics and hypnotic agents. Anxiolytics produce a restful state of mind without interfering with normal mental or physical functions. In allopathic treatment, Benzodiazepines category of drugs like Diazepam, Lorazepam, etc. were most commonly used for anxiety disorders. They have good anxiolytic property but show a high tendency to produce amnesia effect both in animals and human subjects. The alternatives used are Azapirones, however these drugs produce both psychological and physical dependence with withdrawal symptoms. To overcome these effects several herbal remedies like kava, passion flowers, valerian, chamomile, lavender, lemon balm etc. had been studied as alternative treatment for anxiety. But these products have limitations of their own. Some may even cause severe side effects like liver damage, confusion, memory decline etc. (Roth et al., *J. Clinical Pharmacol.* 1984; 18(1 S), 45S-49S). It has been observed that general anxiolytic drugs currently in use have significant adverse effect on the memory of the subject including memory loss or memory impairment.

Sleep disorders are some of the most prevailing health issues around the world, which are very often related to anxiety, stress and depression. Humans sleep approximately one-third of their lives. Though the science of sleep has not fully understood the necessity for sleep and its mechanisms for sleep's physical and mental restoration, sleep disruption or sleep disorders have shown to create fatigue and suboptimal performance causing significant medical, psychological, and social disturbances. Insomnia, the sleep disorder, can be defined as the subjective complaint of impairment in the duration or quality of sleep, characterized by difficulty in falling asleep, difficulty in maintaining sleep, early morning wakening etc. Approximately 35% of the adult population has reported to have insomnia, with chronic problems to nearly 7% leading to anxiety and depression.

Black cumin (*Nigella sativa*) seeds and black cumin seed oil prepared by a cold-press method such as an 'expeller' are being widely used over centuries for the treatment of various ailments throughout the world. It is one of the important drugs in the Indian traditional systems like Ayurveda and Unani. Many studies on *N. sativa* suggest that, its biological activity is attributed specifically to the components in the essential oil. So far, many active compounds have been identified and isolated from black cumin seeds. (Ahmad A. *Asica Pac J Trop Biomed.* 2013; 3(5): 337-352). The oil from the seed is used as a natural protective and curative remedy. *N. sativa* was reported to contain >30% fixed oil and <0.45% volatile oil. One of the major active constituents present in black cumin seed essential oil is thymoquinone which constitutes about 30-48%, p-cymene (7-15%), carvacrol (6-12%), 4-terpineol (2-7%), t-anethole (1-4%), sesquiterpene longifene (1-8%), etc. Thymoquinone (TQ) which is chemically called as 2-isopropyl-5-methyl-1,4-benzoquinone, is the most pharmacologically active compound found in black cumin oil (Salim et al., *Molecules*, 2013; 18(9), 11219-11240). The oil also contains many saturated and unsaturated fatty acids such as linoleic acid, linolenic acid, oleic acid, etc along with alkaloids, Isoquinoline alkaloids (nigellicimine and nigellicimine-N-oxide) and Pyrazol alkaloids or indazole ring bearing alkaloids (nigellidine and nigellicine).

Many toxicological studies have been carried out on *N. sativa* seeds and its oil and no toxic effects were reported. *N. sativa* seed powder does not produce any toxic effects even at very high doses (28 gm/kg orally) in rabbits; its oil was also found safe when given orally to rats ($LD_{50}$ of 28.8 mL/kg). Thymoquinone (TQ), one of the active components in black cumin was usually found in the oil fraction at very low levels of 0.05 to 0.2% w/w. It was found relatively safe when given orally to experimental animals. The $LD_{50}$ of TQ was found to be 104.7 mg/kg and 870.9 mg/kg in mice followed by an intra-peritoneal injection and oral ingestion respectively. Whereas, $LD_{50}$ in rats was found to be 57.5 mg/kg and 794.3 mg/kg after intra-peritoneal injection and oral ingestion respectively (Al-Ali, et al, *J. Ayub. Med. Coll. Abbottabad*, 2008, 20: 252-257). TQ was also reported to be safe in rabbits with an $LD_{50}$ of 2.4 g/kg (Randhawa, *J. Ayub. Med. Coll. Abbottabad.* 2008, 20, 1-2).

Existing technologies for extracting thymoquinone containing oil from matured black cumin seeds had various disadvantages like poor yield, use of organic solvents like hexane, chlorinated solvents, methanol, ethyl acetate, etc. Solvents used in the process will further tend to degrade the thymoquinone fractions and make its concentration low. Technologies discussed in the prior-art report poor thymoquinone content of 0.01-0.2% in the extracted oil. These ordinary black cumin seed oil compositions have been reported to produce anti-anxiety activity at a high dose of not less than 3 grams/day or above, however there is no evidence of studies related to its effect on sleep disorders with simultaneous enhancement in the memory of the subject.

U.S. Pat. No. 8,501,250B2: This invention refers to extractions of fixed oil and thymoquinone rich fractions, (containing up to 6% of thymoquinone) from *Nigella sativa* seeds using supercritical fluid extraction process. However, the invention has not given any details for the preparation of more than 6% thymoquinone containing oils or about its stability and methods for the preparation of stable compositions of thymoquinone rich black cumin extracts in oil and powder form. The invention has also not provided any therapeutic effect on anxiety related disorders and memory enhancement or safety have not been studied.

US 2011/0076346A1 discloses supercritical extraction of black cumin seeds to prepare oil fractions containing 0.01 to 40% thymoquinone and its antioxidant, thermogenic, anti-inflammatory effects. However, the invention has not provided any input regarding the yield of thymoqunine rich fractions of oil that can be produced by the present method. The invention also reported a low percentage thymoquinone content (2.95%) at 100 g level and 39.3% at 100 Kg under same conditions of process. However, no explanation has been given for this unexpected thymoquinone recovery at higher scale, which usually not common. The invention provided a method of just physical blending of thymoquinone rich oil with the powder of the spent material obtained after supercritical extraction. However, no information about its stability is provided, since thymoquinone is a component of the volatile fraction of the oil and is highly oxidisable. Moreover, no information about its brain health functions, or mechanism of action or dosage is provided.

WO2015/086239A1 is directed to thymoquinone or thymoquinone comprising compositions for use in the treatment of neurodegenerative diseases such as Parkinson, Huntington and Alzheimer's disease, however there is no indications for the use of said compositions in combination with anxiolytic properties.

WO2010/133574A1 describes the invention of *N. sativa* oil derived compounds like thymoquinone for the use as an opioid receptor stimulating compound for the treatment or prevent food allergy. The invention has used lipid extract of black cumin containing only 0.22% (w/w) of thymoquinone. No information regarding its process of manufacturing, other composition of the lipid fraction under investigation, safety features, and plausible effects of high thymoquinone fractions were mentioned.

WO2010/050794A1 describes the invention of antioxidant *N. sativa* oil fraction for the treatment of hypercholesterolemia, as demonstrated by the in vitro and in vivo effects of anti-atherogenic, anti-hypolipidemic activities. No information regarding its thymoquinone content, composition, etc are available.

US2012/0244234A1 discloses the use of *N. sativa* extracts for the treatment of symptoms connected to impaired neurotransmission in animals and humans and their use as food/feed supplements. Though the patent has pointed out the serotonin-reuptake inhibition effects of black cumin oil containing 0.01% thymoquinone, and its plausible positive effects on people who are under chronic or acute stress, no information has given on the effect of thymoquinone content or about the process of manufacture of high thymoqunone rich oils and its possible stable formulations and further applications to brain health including sleep disorders. Moreover, they have used an organic solvent extraction process to prepare the oil. The patent has not revealed any suitable composition of the *N. sativa* seeds or its method of preparation or its safety profile for the use of brain health functions, especially with regard to anxiolytic effects with memory enhancement. It does not provide any quantitative data or measurement of its effectiveness in animal or human models to prove its efficacy.

US2001/0076346A1 describes supercritical fluid extracts containing 0.01 to 40% w/w of thymoquinone and their antioxidant, thermogenic, anti-inflammatory activities as useful as nutraceutical supplements for conditions that include obesity, asthma, hypertension, diabetes, inflammation, cough, bronchitis, head ache, eczema, fever, dizziness etc. However, no information regarding the most effective composition for optimum brain functions such as sleep disorders, depression, cognition impairment, stress, anxiety etc have been mentioned.

US2008/0152736A1, US2003/0060454A1, US2003/0060508A1, US2005/0214241A1 describe an invention related to a lipid composition of black cumin to treat/prevent skin infections, wounds, bacterial infections, respiratory diseases, cellulite, cardiovascular diseases, septic infections etc. The invention includes the fractionation of oils into saturated, unsaturated, glycerol esters, volatile fractions etc. and its topical formulations. No information regarding thymoquinone or its neurological effects has been given.

US2002/0132019A1 describes a sterol fraction of black cumin oil and its applications in fungal and bacterial infections, vaginal diseases and disorders by making use of its anti-inflammation, pain reliving or anti-allergic properties.

U.S. Pat. No. 6,218,434B1 describes the use of *N. sativa* derived thymoquinone and dithymoquinone in the treatment of parental and multi-drug resistant human cancers.

Chemically synthesised thymoquinone has been reported to produce memory improvement in a dose dependent manner (Roghani et al. *Pejouhandeh*. 2012; 17(5): 219-227). However it has also been observed that a high dosage of thymoquinone produces toxicity and is harmful to human beings. However, no information on black cumin or its possible effects on brain functions were disclosed.

Hence there exists a need to develop a green process for the extraction of thymoquinone rich black cumin seed oil suitable for safe and convenient oral delivery at 50 to 250 mg dose/day to produce satisfactory efficacy on human subjects experiencing anxiety, stress, depression, sleep disorders, memory decline etc. It has been anticipated that extract compositions comprising thymoquinone at about 2 to 45% w/w and preferably about 2 to 25% w/w, more preferably 2 to 10% may be of great use. There also exists a need to develop a safe herbal nutraceutical composition based on thymoquinone rich black cumin seed oil, effectively useful for the treatment of anxiety conditions, which also exhibits simultaneous memory enhancement effect.

SUMMARY OF THE INVENTION

The current invention discloses compositions derived from black cumin seeds which comprises high concentrations of thymoquinone, and a green process for the preparation of thymoquinone rich black cumin seed compositions in oil and free flowing powder form, to effectively manage anxiety disorders with simultaneous memory enhancement effects.

One embodiment of the current invention is a biologically active black cumin seed extract in liquid oil form or water soluble free flowing powder form, wherein it comprises thymoquinone, α-linoleic acid and polyphenols.

One embodiment is the biologically active black cumin seed oil extract liquid, wherein it comprises thymoquinone at a concentration of 0.5 to 43%, α-linoleic acid in the range of 45-60% and polyphenols in the range 0.1 to 4% as gallic acid equivalent.

One embodiment of the current invention is the biologically active black cumin seed extract in the water soluble free flowing powder form, wherein it comprises thymoquinone in the range of 0.5-8% and α-linoleic acid at a concentration of 1 to 10%, and wherein it further comprises 10-50% proteins and 20-70% carbohydrates.

In one embodiment it comprises α-linoleic acid at a concentration of 1-60%, thymoquinone at a concentration of 0.5-45%, polyphenols, proteins, and carbohydrates.

One embodiment of the current invention is a pharmaceutical formulation comprising the composition disclosed herein and a pharmaceutically acceptable carrier, wherein the pharmaceutical composition can be administered orally at a dose in the range of 50 to 500 mg per day, for treating memory, stress, anxiety and sleep associated disorders in patients, and wherein the pharmaceutical composition comprises not less than 5% thymoquinone and not less than 45% α-linoleic acid.

In one embodiment, the pharmaceutical formulation has anxiolytic effect on humans. In one embodiment, it can be given as a nutraceutical supplement for humans to enhance memory.

In one embodiment, it can be used in patients with memory loss disorders. In one embodiment, it can be used to treat sleep disorders in patients with sleep disturbances or high sleep latency (individuals who take long time to get into sleep high sleep latency)

In one embodiment, it acts by inhibiting acetyl cholinesterase.

In one embodiment, it does not have any adverse effects in the patients at the prescribed dose.

One embodiment of the current invention is a process for preparing a biologically active black cumin seed extract in free flowing powder form using black cumin seeds, the process comprising steps of:

(a) pre-treating powdered or flaked black cumin seeds with enzymes, followed by supercritical carbon dioxide extraction of the oil from the seeds to obtain a super critical extracted oil fraction which comprises non-volatile fixed oils rich in α-linoleic acid and volatile oils rich in thymoquinone and containing polyphenols, (b) extracting the residual black cumin seed material left after step (a) with a hydrophilic solvent to obtain residual black cumin seed extract;

(c) spray-drying the residual black cumin seed extract from step (b) to obtain a residual black cumin seed free flowing powder;

(d) dissolving the residual black cumin seed free flowing powder from step (c) in water to obtain a residual black cumin seed extract solution at 10-25% total dissolved solids level;

(e) mixing the supercritical extracted oil fraction from step (a) with the residual black cumin seed solution obtained step (d), followed by homogenization or ultrasonication of the mixture thus obtained to produce an emulsion; and (f) spray-drying or freeze drying the emulsion from step (e) to obtain black cumin seed extracted oil composition in free flowing powder form, wherein the black cumin seed extracted oil composition in water soluble free flowing powder form comprises thymoquinone at the concentration of 0.1 to 8%.

In one embodiment, the hydrophilic solvent used for extraction in step (b) is water or a mixture of water and ethanol or methanol. In one embodiment, the step (b) of extracting the residual black cumin seed material using a hydrophilic solvent is done by usual methods of solvent extraction at 50 to 60° C.

One embodiment of the current invention is a process for preparing biologically active black cumin seed extract in liquid oil form using black cumin seeds, the process comprising steps of:

(a) pre-treating the powdered or flaked black cumin seeds with water to form a slurry and further treating the slurry with at least one enzyme;

(b) drying the slurry to the powder form with 3 to 6% moisture level (c) extracting the liquid oil by supercritical carbon dioxide extraction from the dried powder from step (b), wherein the black cumin seed extract in the liquid oil form comprises thymoquinone at the concentration of 2-43%.

In one embodiment, the pre-treatment with the at least one enzyme in the processes disclosed herein, is done for 1-8 hours.

In one embodiment, the at least one enzyme is selected from the group consisting of pectinase, amylase, galactosidase and protease. In one embodiment, the supercritical extraction of black cumin seeds is performed using carbon dioxide, and the extraction pressure of the carbon dioxide gas is in the range of 100 to 220 bar, and extraction temperature is in the range of 35 to 50° C.

BRIEF DESCRIPTION OF THE FIGURES

FIG. 1 illustrates process flow of Black cumin seed extraction.

DETAILED DESCRIPTION OF THE INVENTION

Figure 2A:
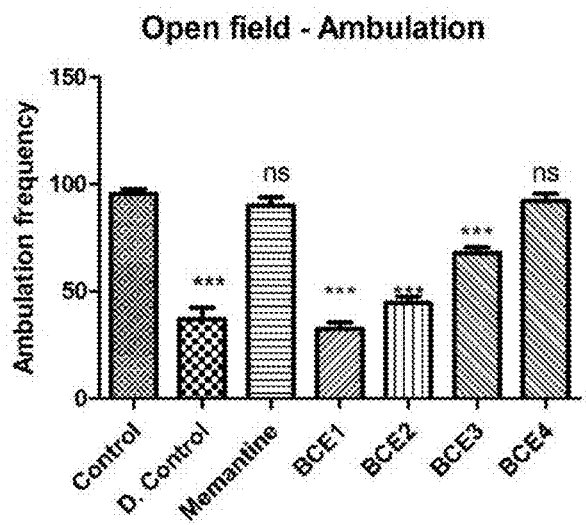
FIG. 2a shows effect of BCE compositions in open field test to demonstrate the ambulation frequency of animals.

The terms "BCE", "black cumin seed extract", "black cumin seed powder compositions", constitutes same meaning, are being used interchangeably throughout the document.

The current invention discloses compositions derived from black cumin seeds which comprises high concentrations of thymoquinone, and a green process for the preparation of thymoquinone enriched black cumin seed compositions in oil and free flowing powder form, to effectively manage anxiety disorders with simultaneous memory enhancement effects.

One embodiment of the current invention is a biologically active black cumin seed extract in liquid oil form or water soluble free flowing powder form, wherein it comprises thymoquinone, α-linoleic acid, and polyphenols.

One embodiment is the biologically active black cumin seed extract is in liquid oil form, wherein it comprises thymoquinone in the range of 0.5 to 43%, and α-linoleic acid in the range of 45 to 60% and 0.1 to 4% polyphenols as gallic acid equivalent.

One embodiment of the current invention is the biologically active black cumin seed extract in the water soluble free flowing powder form wherein it comprises thymoquinone at a concentration of 0.5 to 8% and α-linoleic acid at a concentration of 1 to 10%, and wherein it further comprises 10 to 50% proteins and 20 to 70% carbohydrates. In one embodiment it comprises α-linoleic acid at a concentration of 1-60%, thymoquinone at a concentration of 0.5 to 45%, proteins, and carbohydrates. The carbohydrates and proteins in the composition are obtained from the black cumin during the extraction process. The carbohydrates and proteins are not being added from any other external sources.

One embodiment of the current invention is a pharmaceutical formulation comprising the composition disclosed herein and a pharmaceutically acceptable carrier, wherein the pharmaceutical formulation can be administered orally at a dose in the range of 50 to 500 mg per day, for memory enhancement, stress, anxiety and sleep associated disorders in patients, and wherein the pharmaceutical formulation comprises not less than 5% thymoquinone and not less than 45% α-linoleic acid. In one embodiment, the pharmaceutical formulation has anxiolytic effect on humans.

In one embodiment, it can be given as a nutraceutical supplement to humans to enhance memory.

In one embodiment, it can be used in patients with memory loss disorders. In one embodiment, it can be used to treat sleep disorders in patients with sleep disturbances or high sleep latency (those who takes long time to get into good sleep). In one embodiment, it acts by inhibiting acetyl cholinesterase. In one embodiment, it does not have any adverse effects in the patients at the prescribed dose.

In one embodiment, the black cumin extract composition in the oil is administered in the range of 50-500 mg to provide desired therapeutic effect. In one embodiment, the black cumin extract composition in powder form is administered in the range of 50-500 mg to provide desired therapeutic effect.

One embodiment of the current invention is a process for preparing a biologically active black cumin seed extract in free flowing powder form using black cumin seeds, the process comprising steps of: (a) pre-treating powdered or flaked black cumin seeds with enzymes, followed by supercritical carbon dioxide extraction of the oil from the seeds to obtain a super critical extracted oil fraction which comprises non-volatile fixed oils rich in α-linoleic acid and volatile oils rich in thymoquinone; (b) extracting the residual black cumin seed material left after step (a) with a hydrophilic solvent to obtain residual black cumin seed extract; (c) spray-drying the residual black cumin seed extract from step (b) to obtain a residual black cumin seed free flowing powder; (d) dissolving the residual black cumin seed free flowing powder from step (c) in water to obtain a residual black cumin seed extract solution at 10 to 25% total dissolved solids level; (e) mixing the supercritical extracted oil fraction from step (a) with the residual black cumin seed solution obtained step (d), followed by homogenization or ultrasonication of the mixture thus obtained to produce an emulsion; and spray-drying or freeze drying the emulsion from step (e) to obtain black cumin seed extracted oil composition in free flowing powder form, wherein the black cumin seed extracted composition in water soluble free flowing powder form comprises thymoquinone at the concentration of 0.1 to 8%. In one embodiment, the hydrophilic solvent used for extraction in step (b) is water or a mixture of water and ethanol. In one embodiment, the step (b) of extracting the residual black cumin seed material using a hydrophilic solvent is done by usual methods of solvent extraction at 50 to 60° C.

One embodiment of the current invention is a process for preparing biologically active black cumin seed extract in liquid oil form using black cumin seeds, the process comprising steps of: (a) pre-treating the powdered or flaked black cumin seeds with water to form a slurry and further treating the slurry with at least one enzyme; (b) drying the slurry to the powder form with 3 to 6% moisture level (c) extracting the liquid oil by supercritical carbon dioxide extraction from the dried powder from step (b), wherein the black cumin seed extract in the liquid oil form comprises thymoquinone in the range of 2-43%.

In an embodiment, the pre-treatment of black cumin seeds with enzymes improves the efficiency of the extraction process.

In yet another embodiment, the enzymes used for the methods disclosed in the current invention can be pectinases, galactosidases, proteases or any combination thereof. In one embodiment, the enzymes are selected from the group of, but not limited to 100 to 1000 ppm pectinase, 100 to 1000 ppm galactosidase, 100 to 1000 ppm protease or any combinations thereof. In one embodiment, the pre-treatment with the at least one enzyme in the processes disclosed herein, is done for 1 to 8 hours.

In one embodiment, the supercritical extraction of black cumin seeds is performed using carbon dioxide, and the extraction pressure of the carbon dioxide gas is in the range of 100 to 220 bars, and extraction temperature is in the range of 35 to 50° C.

In one embodiment, the supercritical extraction of black cumin seeds is performed using carbon dioxide ($CO_2$). The extractor vessel is loaded with powdered material of black cumin seeds. $CO_2$ gas is delivered to the extraction vessel using a high pressure pump and the extraction pressure is varied from 60 to 250 bar and temperature is varied from 30-70° C. The pressure in the extraction vessel is controlled by back pressure regulator and temperature is controlled by chilled water. Heat exchangers are provided in the system to maintain temperature at the extractor and separator vessel. The oil is collected from the separator vessel at definite time intervals by releasing the pressure. In the next step the extracted oil is filtered through a filter cloth. The volatile oil fractions were further separated to provide thymoquinone rich black cumin seed oil with thymoquinone content of about 2 to 45% w/w, preferably about 2 to 25% w/w or 2 to 10% (w/w).

In one embodiment, the spent raw material after supercritical extraction is extracted with a hydrophilic solvent. In one embodiment, the hydrophilic solvent is water. In one embodiment, 1 kg of the spent material is mixed with 1:2 to 1:5 w/v of water. In one embodiment, this mixture is then stirred at 50 to 60° C. and the solution is cooled and filtered. The filtrate is concentrated using a vacuum evaporator and then spray dried or freeze-dried to get free flowing powder.

In one embodiment, the powder is further subjected to nutritional analysis to check its protein, carbohydrates and fat content. In one embodiment, the compositions made using the processes disclosed in the current invention are subjected to qualitative analysis, such as nutritional analysis to determine their composition, such as content of thymoquinone, proteins, carbohydrates and linoleic acid.

In one embodiment, the powder is dissolved in water at 10 to 25% dissolved solid level. In one embodiment, the supercritical extracted oil fraction rich in thymoquinone is mixed and homogenized using a high pressure homogenizer. The emulsion thus obtained is spray dried or freeze dried to get stable encapsulated oil extract powder in the natural black cumin seed matrix, without any added excipients or organic solvents.

In one embodiment, the presence of enriched thymoquinone content in said black cumin extract alleviates anxiety related disorders and exhibits significant enhancement on memory of the subject, without causing any toxicity. Due to this high concentration of thymoquinone fractions in the black cumin seed oil composition, it can be effectively used at lower dosages, for example about 50 mg to 250 mg/day to achieve said therapeutic effects.

In one embodiment, the current invention discloses health protective nutraceutical compositions, more particularly to a process for preparing black cumin seed extract composition having significant therapeutic properties to treat anxiety, stress and sleep disorders along with significant memory enhancement. In on embodiment, the processes disclosed herein are "green", and don't involve the use of any organic solvents.

In one embodiment, the primary objective of the present invention is to develop a green process for the preparation of thymoquinone rich black cumin seed oil, having thymoquinone concentration of about 2 to 45% (w/w) and preferably about 2 to 25% (w/w), more preferably about 2 to 10% (w/w) to effectively manage anxiety disorders with simultaneous memory enhancement effects.

In another embodiment the compositions of present invention provide optimum nutrition for the protection and promotion of brain functions on people having sleep disorders of various types, especially due to age, depression, fatigue, stress, anxiety, and long travel.

Another embodiment of the present invention is to have a safe black cumin derived extract composition which helps to have a fast and sound sleep without compromising on memory.

In an embodiment, the black cumin seed composition inhibits effect on Acetylcholesterase and to maintain healthy acetylcholine levels in brain. In an embodiment, the black cumin seed composition having antagonistic activity against glutamate receptors, more specifically to the receptor subtype NMDA for anxiolytic effects.

In another embodiment of the present invention, a novel and safe composition of phytochemical(s) from the black cumin seeds are provided, which possess significant brain health beneficial pharmacological effects by modulating neurotransmitters levels.

In yet another embodiment a unique composition of black cumin seeds is developed containing fatty acids with more than 1 to 60% α-linoleic acid, 2 to 45% thymoquinone, with relatively low levels polyphenols in oil and free flowing powder or granule form suitable for dietary supplement or food applications as an ingredient.

In yet another aspect of the present invention a formulation is provided from the lipophilic oil extract of black cumin seeds as water soluble powder form with minimum 5% thymoquinone, wherein the formulation is made without using any excipients or organic solvents other than the extracts of black cumin seeds.

In one embodiment of the present invention an enzyme-assisted supercritical fluid extraction procedure is provided to produce thymoquinone rich fractions of black cumin oil in a single step without further fractionations and to provide a unique composition having the sleep order benefits, as a novel method of preparation.

In another embodiment of the present invention, a process for preparing black cumin seed oil with enriched amount of thymoquinone, preferably about 2 to 45% w/w and more preferably about 2 to 25% w/w, more particularly 2 to 10% without altering any vital functions. Present invention further provides a composition of thymoquinone rich black cumin seed oil, used as an effective agent against anxiety related disorders and exhibits simultaneous improvement in memory of the subject.

The extraction process involves an enzyme assisted pre-treatment of the seeds followed by a supercritical carbon dioxide extraction without using any solvents. Black cumin seed oil containing fractions such as fatty acids, polyphenols, thymoquinone, dithymoquinone etc. are obtained in high yield. In one embodiment, the oil extract comprises components having not less than 50% w/w of α-linoleic acid, about 2 to 45% w/w thymoquinone or preferably about 2 to 25% w/w thymoquinone, and 0.1 to 4% polyphenols as gallic acid equivalent.

One embodiment of the present invention is to provide the unique black cumin seed extracted oil composition in biologically active free flowing powder form suitable for 50 to 500 mg optimized dosage forms, with standardized levels of thymoquinone, α-linoleic acid and polyphenols, for safe human consumption to relieve or to treat sleep disorders and related problems.

In one embodiment, the compositions disclosed herein can be administered orally to patients/subjects requiring them.

In one embodiment, the solid dosage forms for oral administration may include capsules, soft gel capsules, tablets, sublingual tablets, powders, granules and gels.

In one embodiment the liquid dosage forms for oral administration can include pharmaceutically acceptable emulsions, solutions, suspensions, and syrups.

The term "sleep latency" or sleep onset latency" as defined herein refers to the time taken to transition from full wakefulness to any stage of sleep.

The term "high sleep latency" as used herein, is defined as more than usual time taken for onset of sleep. This can be a stage or preliminary stage of insomnia.

Sleep homeostasis refers to the regulatory mechanism that maintains an overall constancy of sleep intensity and duration. Sleep deprivation creates a sleep debt that must be repaid, resulting in compensatory heightened pressure to sleep and eventual increased sleep intensity and duration. Conversely, excessive sleep reduces sleep propensity and amount of sleep.

Sleep physiology changes with age as the brain matures and eventually degenerates. With advancing age, there is a decline in the percentage of sleep that is deep, more frequent awakenings, and sleep fragmentation. In the elderly, sleep disorders such as obstructive sleep apnea (OSA) occur more frequently. Sleep needs also vary with age, decreasing from 16 hours a day in infancy and stabilizing at 7½ to 8 hours for most normal adults.

Insomnia is the most prevalent sleep disorder and affects large proportions of the population on a situational, recurrent, or persistent basis.

In one embodiment, the novel compositions disclosed herein can be used to treat or prevent sleep disorders or memory-loss associated symptoms.

Treating and preventing sleep disorders or memory-related symptoms" includes eliminating or curing the sleep disorder or, reducing the severity of the symptoms (e.g., compared to the severity of the disorder/symptoms before the compounds or compositions of the present invention were administered), and/or reducing the rate of progression of the disorder/symptom severity (e.g., compared to the rate of progression in the absence of the compounds or compositions of the present invention).

Anxiety is a mood of fear, worry, and uneasiness resulting from the apprehension of something bad happening and has widespread deleterious social consequences. While anxiety can be a normal beneficial response to events that truly threaten ones security, chronic and irrational anxiety in response to normal life events in the absence of genuine threats can be debilitating and is considered to be an anxiety disorder. Anxiety disorder rates can be as high as 30 to 40% of the population.

In one embodiment, the compositions disclosed herein have anxiolytic properties when administered to humans. In one embodiment, the compositions disclosed herein have anxiolytic effects by effecting GABA pathways.

It should be understood that the detailed description and specific examples, while indicating embodiments of the invention, are given by way of illustration only, because various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention.

The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate; meaning that the term "around", "about" or "approximately" can be inferred if not expressly stated.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "non-volatile fixed oils" as used herein is defined as the oil which consisted of volatile components, other than the oil components such as fatty acids and their esters.

The term "green process" as used herein means an "eco-friendly process" which does not use any organic solvents.

The term "pharmaceutical formulation" as used herein is defined as a formulation that can be administered to a patient for treating/preventing a disease and/or symptoms. The pharmaceutical formulation may comprise pharmaceutically acceptable salts, or carriers, or flavours.

EXAMPLES

Example 1: Supercritical Fluid Extraction (SCF) of Black Cumin

Matured and dried black cumin seeds were flaked in a double roller grooved flaker with a flake thickness maintained at 0.2 to 0.5 mm. It is pulverized in a hammer mill to the particles of 0.05 to 0.25 mm. Then 5 kg of raw material (RM-Black cumin seed powder) is charged in to the SCF extractor and extraction is conducted at pressures between 100 bar to 220 bar using micro filtered $CO_2$. The $CO_2$ is initially drawn from cylinders and chilled in a chiller unit working between 3.5° to 6.5° C. and further pressurized using plunger pump where the $CO_2$ is made to liquid form at its supercritical stage. The liquid $CO_2$ is pumped to the extractor. The extraction process is conducted at 42±2° C. and the extract was collected at various pressures as shown in Table 1. The extract is obtained as a mixture with $CO_2$ and the moisture. The mixture is collected in a separation chamber which is maintained at 70° C. using water jacket, where $CO_2$ is separated and sent back to the chiller unit in gaseous form. The liquid product and moisture is collected from bottom of the separator and tapped out of the system. The extract is passed through anhydrous sodium sulphate for removing moisture. Moisture-free oil thus obtained at various conditions were analysed and blended to produce black cumin oil extract containing various percentage of thymoquinone ranging from 1 to 30% (w/w), more particularly to 1, 2, 5, 10, 20 and 25% with 0.5 to 4% polyphenols. The thymoquinone content in oil obtained at various pressure levels are outlined in Table-1.

Example 2: Enzyme Assisted Supercritical Extraction of Black Cumin Seeds

About 5 kg of black cumin seeds are flaked and grinded as above, to a particle size of 0.05 to 0.25 mm. The black cumin powder is made into a slurry with water in the ratio of 1:2 to 1:4 w/v. It slurry is then treated with a mixture of enzymes, preferably containing pectinase and amylase at pH 4.5 to 5.5 at 50° C. for 6 to 8 h. It is then subjected to ultrasonication for 30 to 90 min using a 1000 W ultrasound generator. The slurry was then dried to less than 6% moisture content under vacuum. The dried powder was then subjected to super critical extraction as by using the process discussed in Example 1.
The Table-1 below illustrates the sequential SCF extraction of black cumin seeds at various pressures and the thymoquinone content obtained by said process

TABLE 1

Oil extract content at various pressures

| Pressure (Bar) | Yield of extract (%) | | Thymoquinone content (%) | | Linoleic acid content (%) |
| --- | --- | --- | --- | --- | --- |
| | Direct SCF extraction | Enzyme-assisted SCF-extraction | Direct SCF extraction | Enzyme-assisted SCF extraction | |
| 100 ± 2 | 0.2 | 0.3 | 32 ± 5 | 43 ± 3 | 48 |
| 150 ± 2 | 1.3 | 1.5 | 5.9 ± 3 | 7.6 ± 2 | 51.4 |
| 180 ± 2 | 1.8 | 2 | 1.7 ± 2 | 2.2 ± 2 | 52.7 |
| 220 ± 2 | 22 | 28 | 0.16 ± 0.4 | 0.18 ± 0.5 | 46.3 |

Example 3: Water Extraction of the Spent Black Cumin (De-Oiled Black Cumin) after Supercritical Extraction Dried spent black cumin (10 kg) is charged into an extraction vessel fitted with a water circulation pumps, agitator and heating facility. Water (40 L) is added into the extraction vessel as solvent and agitated at 200 to 500 rpm for 2 h along with water circulation at 50 to 60° C.
The water extract was filtered and stored in a separate tank. A second extraction and third extraction were repeated in the same way and the filtered water extract are mixed together. The mixture is then evaporated under vacuum at 50 to 60° C. to a brix level (total dissolved solids level) of 20 to 30% and further blended with 5 to 10% (w/w) of excipients such as maltodextrin, starch or gum acacia. The mixture was homogenised and spray dried at inlet temperature of 85 to 95° C. and outlet temperature of 140-160° C. The fine powder thus obtained was found to contain a thymoquinone content of 0.2 to 5% (w/w). The same procedure can also be carried out without external carriers such as maltodextrin, starch or gum acacia.

Example 4: Encapsulation of Supercritical Extracted Black Cumin Oil (BCO) with Water Extract Calculated quantity of black cumin oil containing high levels of thymoquinone (TQ) (prepared in Example 1 or 2) is added to a water solution of gum acacia or modified starch and homogenised at high pressure of 400 to 1000 bars. The resulting micelles with 1 to 2 µm (micro meter) particle size were further added to the water extract concentrated to a total dissolved solids level (brix) of 20 to 30% (w/w). The solution is homogenised once again and spray dried. The free flowing powders obtained contains 0.5 to 8% of thymoquinone.

Example 5: Cold Press Method of Black Cumin Oil Preparation

Dried black cumin seeds are pressed (expelled) at room temperature (25° C.) by mechanical pressing without any heat treatment. Commercially available expellers used for expelling seeds like sesame can be used for the purpose. Crushed seeds are stored for one night at room temperature to separate oil phase from fiber, and then oil was filtered using nylon filter cloth and a funnel. The resulting oil was found to contain 0.24% thymoquinone.

Example 6: Analysis of Thymoquinone Content

Thymoquinone content is analysed using high pressure liquid chromatography (HPLC). Thymoquinone concentration in oil is measured based on the calibration curve prepared using the analytical standard of thymoquinone collected from Sigma-Aldrich, USA. Oil is dissolved in isopropanaol (IPA) for injection. Mobile phase is (90:10 (v/v) mixture of water/IPA as solvent A and Methanol as solvent B under gradient elution. Detection was carried out at 254 nm at 1 mL/min. Reverse phase column (Phenomenex, 250×4.6 mm, 5 µm) was employed.

Example 7: Fatty Acid Analysis of Black Cumin Oil

Fatty acids were analysed as per the method disclosed in Gharby et al, *J Saudi Society of Agricultural Sciences*, 2015, 14(2), 172-177. Fatty acid methyl esters (FAMEs) are analyzed by gas chromatography using a Varian CP-3800 (Varian Inc.) chromatograph equipped with a FID. A split injector is used and the injected volume was 1 µL. The column used is a CP-Wax 52CB column (30 m×0.25 mm i.d.; Varian Inc., Middelburg, The Netherlands). The carrier gas is helium and the total gas flow rate was 1 mL/min. The initial and final column temperature was 170 and 230° C., respectively, and the temperature is increased by steps of 4° C./min. The injector and detector temperature is 230° C. Data were processed using a Varian Star Workstation v 6.30 (Varian Inc., Walnut Creek, Calif., USA).

Example 8

Relative stability of black cumin oil powder prepared by (a) by physical mixing of thymoquinone rich oil with the powder of the residual spent black cumin seed material left after supercritical extraction and (b) by encapsulation of thymoquinone rich oil with the water extract powder of the residual spent black cumin seed material left after supercritical extraction. The stability of the powder is evaluated as per the conditions provided below Storage Conditions The black cumin powder (5 g) powder samples are packed in polyethylene covers and stored in a stability chamber in High density polyethylene bottles. The temperature and humidity conditions in stability chamber are maintained at 40° C.±2° C./75%±5% RH. Stability chamber is monitored for temperature and humidity on a daily basis. On analysis of thymoquinone content and other parameters at regular intervals, it is observed that enhanced stability of the encapsulated powder as compared to its physical blend. The stability data as outlines in Table-2a and Table-2b.

TABLE 2a

Table illustrating results of stability data of TQ rich black cumin seed powder by super critical extraction

| Parameters | Specifications | Withdrawal Period | | | | | | |
|---|---|---|---|---|---|---|---|---|
| | | 0 month | 1 month | 2 month | 3 month | 4 month | 5 month | 6 month |
| Appearance | Free flowing Powder | Complies | Complies | Complies | Complies | Complies | Complies | Complies |
| Odour | Characteristic smell of black cumin | Complies | Complies | Complies | Complies | Complies | Complies | Complies |
| Thymoquinone content | NLT 5% | 5.71% | 5.12% | 4.83% | 4.56% | 4.1% | 3.9% | 3.12% |
| Identification | HPLC | Complies | Complies | Complies | Complies | Complies | Complies | Complies |

TABLE 2b

Table illustrating results of stability data of TQ rich Black cumin oil encapsulated powder

| Parameters | Specifications | Withdrawal Period | | | | | | |
|---|---|---|---|---|---|---|---|---|
| | | 0 month | 1 month | 2 month | 3 month | 4 month | 5 month | 6 month |
| Appearance | Free flowing Granules | Complies | Complies | Complies | Complies | Complies | Complies | Complies |
| Odour | Characteristic smell of black cumin oil | Complies | Complies | Complies | Complies | Complies | Complies | Complies |
| Thymoquinone content | NLT 5% | 5.68% | 5.69% | 5.48% | 5.40% | 5.22% | 5.38% | 5.19% |
| Identification | HPLC | Complies | Complies | Complies | Complies | Complies | Complies | Complies |

Example 9: In Vivo and In Vitro Studies

Further in vivo studies are performed to demonstrate the anxiolytic behaviour of black cumin seed extract compositions with significant memory enhancement I. Evaluation of Memory Enhancement by Thymoquinone Rich Composition of Black Seed Oil by Intra-Cerebroventricular (I.C.V) Injected Ibotenic Acid Model Ibotenic acid (IBO) is a non-selective glutamate receptor antagonist which can be used as a powerful neurotoxin to produce anxiety, stress, depression and dementia. It is injected intra cerebro-ventricularly as a brain lesioning agent specially to destroy the neuronal cells in hippocampal and cortical region responsible for fear, anxiety and depression, as well as learning and memory. It has been proved that IBO neurotoxicity is mediated through the NMDA (N-methyl-D-aspartate) receptor or channel complex, one of the glutamate receptor widely distributed throughout the brain. The NMDA subtype of glutamate receptor is an important mediator of synaptic plasticity and plays a central role in the neurobiological mechanisms of emotionality including fear, anxiety and depression, as well as learning and memory (Barkus et al., *European Journal of Pharmacology*, 2010; 626(1), 49-56).

Albino Wistar rats are randomly assigned into seven groups with five animals each as shown in Table-3. Ibotenic acid is administered to Albino Wistar rats at the dose of 5 µg/µL/intracerebroventricularly using Hamilton syringe at the rate of 0.1 µL/min. The animals were then treated continuously for 30 days with Black cumin extracts (BCE) orally at various dosages (thymoquinone content) and evaluated for its anxiolytic properties using elevated plus maze and modified open field apparatus. The various black cumin extracts (BCE) dosages evaluated in the study are outlined in Table-3.

TABLE 3

Table illustrating experimental design indicating the various groups of animals treated with various compositions of BCE

| Groups | Treatment |
|---|---|
| Group I | Normal control animals. |
| Group II | Rats injected with IBO into hippocampus. |
| Group III | Rats injected with IBO and treated with Memantine at the dose of 5 mg/kg. |
| Group IV | Rats injected with Ibotenic acid and treated with BCE1 0.3% |
| Group V | Rats injected with Ibotenic acid and treated with BCE2 1% |
| Group VI | Rats injected with Ibotenic acid and treated with BCE3 2% |
| Group VII | Rats injected with Ibotenic acid and treated with BCE4 5% |

Open Field Test:

The open field test is conventionally designed to assess the state of anxiety, locomotor and exploratory activity. In open field, the parameters like ambulation (movement) and rearing (tendency of the rats to stand on hind limbs with or without support of the wall) were estimated. FIG. 2*a* shows assessment of ambulation behaviour of wistar rats using open field apparatus. Results were statistically analysed by one-way ANOVA followed by Tukey's multiple comparison test.

The experiment results from FIG. 2a demonstrated the significant improvement in ambulation behaviour by BCE4 containing 5% TQ when compared to the normal cold pressed oil (BCE1) which usually contains 0.2 to 0.3% TQ and also with other samples BCE2 and BCE3. The composition BCE4 produced similar effect as that of the positive control Memantine which was similar to non-treated control animals (p>0.05). It has been proposed that fear response (or anxiety) of the animal exposed to a new and thus potentially dangerous environment is accompanied by low ambulation, especially in the central zone.

Figure 2B:
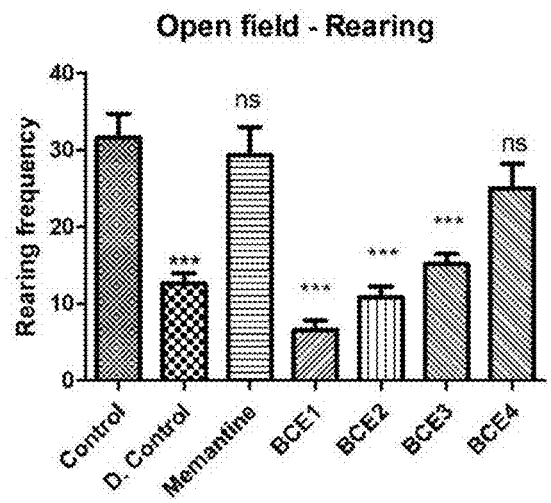
FIG. 2b shows effect of BCE compositions in open field test to demonstrate the rearing frequency of animals

As seen in FIG. 2b (Open field experiment; Rearing, the rearing behaviour in BCE4 treated animals was increased when compared to that of the disease induced group and there was no significant difference between the BCE4 treated group and the control group. The groups BCE3, BCE2 and BCE1 produced increase in rearing frequency when compared to that of disease induced group and did not produced significant activity when compared to that of normal control animal group. The rearing behaviour in BCE4 treated animals were increased when compared to that of the disease induced group and there is no significant difference between the BCE4 treated group, memantine group and the control group (p>0.05), indicating the efficiency of BCE4 composition which contains 5% Thymoquinone and >45% α-linoleic acid. The improvement in rearing behaviour is a measure of reduction of anxiety and stress.

Elevated Plus Maze

The anxiolytic activity was further estimated by using elevated plus maze experiment. The proportion of entries into and time spent on open arms were considered as the parameters. Anxiolytics tends to increase the time spent and open arm entries by reducing the fear response.

Elevated Plus Maze-Number of Open Arm Entries

Figure 3A:
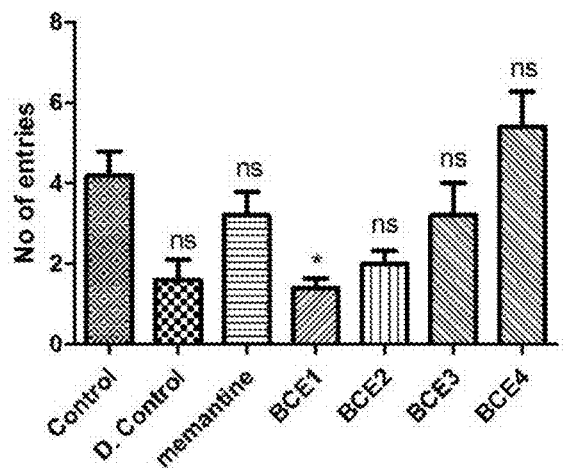
FIG. 3a shows effect of BCE compositions for evaluation of anti-anxiety property using elevated plus maze-number of open arm entries.

In this experiment, BCE4 showed a significant increase in the open arm entries when compared to that of the other groups containing 0.2 (BCE1), 1 (BCE2) and 2% (BCE3) thymoquinone. The entry into the open arm directly corresponds to the anxiolytic property. The activity of BCE4 is followed by BCE3, BCE2 and BCE1 as shown in FIG. 3a. The increase in the open arm entry shows the reduction in the fear response of the animal which shows the anxiolytic property.

Figure 3B:
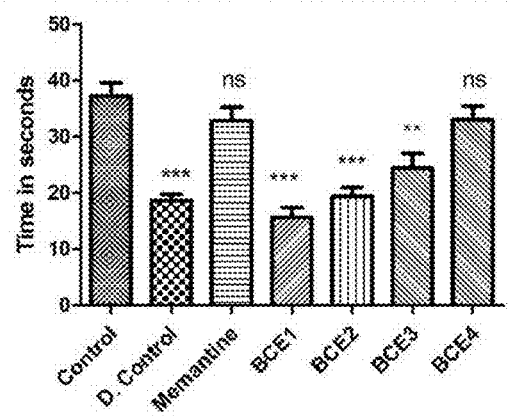
FIG. 3b shows effect of BCE compositions for evaluation of anti-anxiety property using elevated plus maze-Time spent in open arm.

Elevated Plus Maze Experiment—Time Spent in Open Arm:

The continuous treatment with BCE4 showed prominent results in the time spent by the animals in open arm (33±2.429) which was significant when compared to that of disease control group with time of 18.60±1.077. Other groups BCE1, BCE2 and BCE3 cannot produce significant beneficial effect as compared to BCE4 as shown in FIG. 3b. From the above data we can conclude that, the Black Cumin oil with thymoquinone rich (5%) composition of black cumin oil can produce significant anxiolytic activity.

Figure 4A:
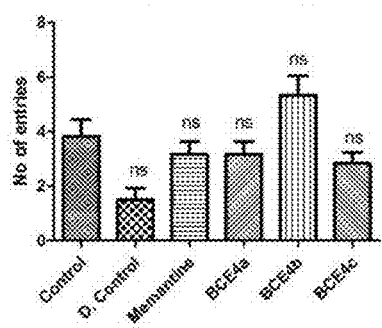
FIGS. 4a and 4b shows effect of BCE compositions on Elevated Plus maze experiment using different doses of BCE4.
Figure 4B:
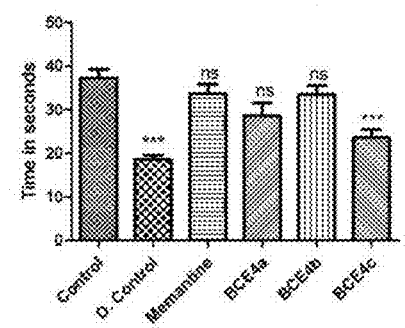

Elevated Plus Maze Experiment—BCE4 at Different Doses:

The elevated plus maze experiment is performed at different doses of BCE4. The activity on number of open arm entries was found to increase on BCE4 treated animals especially at the dose of 5 mg/kg which shows the anxiolytic property as shown in FIG. 4a. BCE4 at the doses of 10 mg/kg and 5 mg/kg significantly increased the time spent in open arm (anxiolytic action) when compared to that of the disease induced animals whereas, BCE4 at the dose of 2.5 mg/kg showed less activity as shown in FIG. 4b. The BCE was found to be effective at the dose of around 5 mg/kg.

II. Evaluation of Memory of Thymoquinone Rich Composition of Black Seed Oil by Scopolamine Induced Model.

Cognitive functions are highly dependent on central cholinergic neurotransmission. Even though, other neurotransmitters too involve in memory process, Acetyl choline (Ach) plays a major role in memory and learning process. Many studies had proved that decline in cholinergic function would lead to memory dysfunction (Blokland A, *Brain Research Reviews*, 1995; 21(3), 285-300)

In our study, Scopolamine, an anti-muscarinic agent was administered intraperitoneally at the dose of 1 mg/kg into Wistar rats to produce amnesia. Scopolamine is a muscarinic receptor antagonist and can pass through blood brain barrier and cause amnesia (memory loss) in animals by blocking cholinergic neurotransmission. The cholinergic neurotransmission was blockaded, leading to cholinergic dysfunction and impaired cognition in rats. This model was selected to study the effect of BCE on Acetylcholine related memory.

The experimental design was planned in a way where BCE could be evaluated after 14 days against Scopolamine induced amnesia. Here, the animals (Albino Wistar rats) were randomly assigned into seven groups containing five animals each as shown in Table-4 below, which shows experimental grouping of animals for evaluation of memory.

TABLE 4

Table showing experimental grouping of animals for evaluation of memory

| Groups | Treatment |
|---|---|
| Group I | Normal control animals |
| Group II | Animals injected with Scopolamine intra-peritoneally (1 mg/kg) |
| Group III | Animals injected with Scopolamine and pre-treated with Piracetam at dose of 100 mg/kg |
| Group IV | Animals injected with Scopolamine and pre-treated with BCE1 |
| Group V | Animals injected with Scopolamine and pre-treated with BCE2 |
| Group VI | Animals injected with Scopolamine and pre-treated with BCE3 |
| Group VII | Animals injected with Scopolamine and pre-treated with BCE4 |

In this study, the animals were pre-treated continuously for 14 days and the end of the study memory related parameters were evaluated using Morris water maze and elevated plus maze (Kulkarni, Kasture, & Mengi, *Indian Journal of Pharmacology*, 2010; 42(3), 168-173) and (Prashar, Gill, & Kakkar, *Pharmacology and Pharmacy*, 2014; 4, 65-76).

Elevated Plus Maze:

In elevated plus maze experiment, the transfer latency is measured which denotes the time taken by the animal at which all its legs have crossed the line into the enclosed arm when it is placed in the closed arm.

Figure 5A:
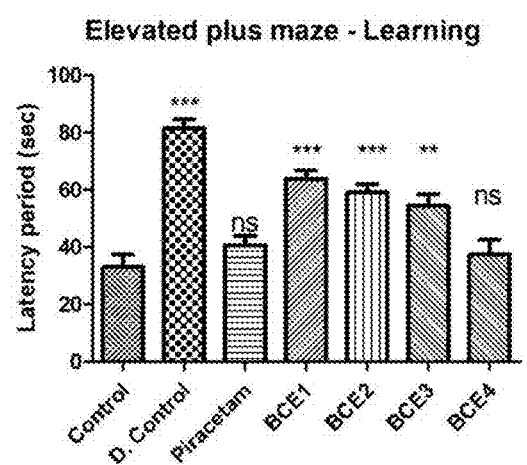
FIG. 5a shows effect of BCE compositions on learning activity by elevated plus maze.

Elevated Plus Maze Experiment—Learning:

The latency time measured during training period is termed as learning activity. Among the seven treated groups, BCE4 showed the less latency period with an efficacy as compared to the standard drug piracetam. Reduction of latency period of BCE4 shows the improvement in learning activity when compared to BCE1, BCE2 and BCE3 with 0.2, 1 and 2% TQ as shown in FIG. 5a.

Figure 5B:
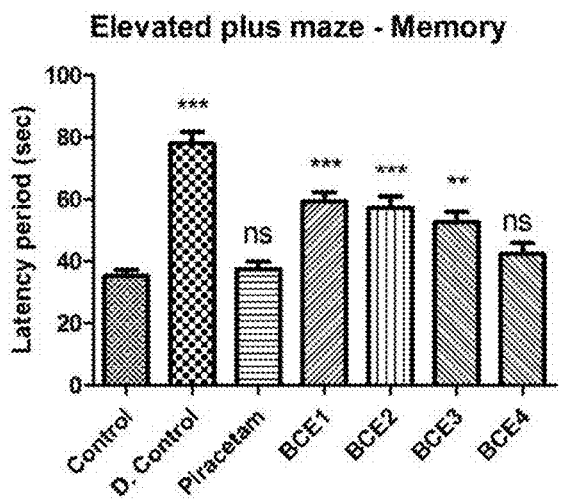
FIG. 5b shows effect of BCE compositions on memory activity by elevated plus maze.

Elevated Plus Maze—Memory:

The measurement in the latency period after 24 h of training represents the memory. The disease induced group showed increased latency period (78±3.728). The animals treated with BCE4 showed the latency period (42.40±3.586) and showed significant difference in activity when compared to that of disease control group. The decrease in latency period by the BCE4 when compared to other BCE's shows the memory improvement among animals treated with only BCE4 composition as compared to BCE1, BCE2 and BCE3 which failed to produce a significant improvement in memory as compared to disease control group. The results as shown in FIG. 5*b*

Figure 6:
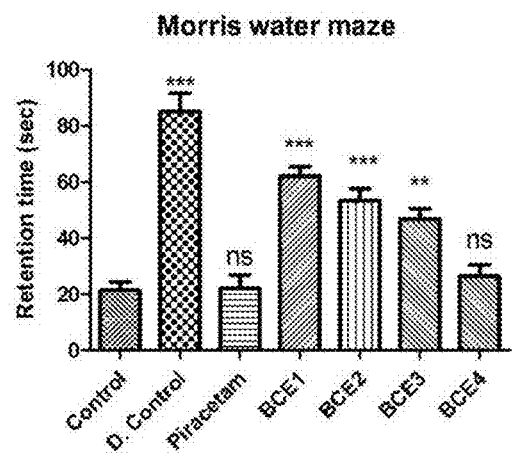
FIG. 6. shows effect of BCE compositions on memory using Morris water maze.

Morris Water Maze Experiment:

In Morris water maze the retention time (time taken by the animal to reach the hidden platform) is measured. Piracetam at the dose of 100 mg/kg is used as standard drug. The animals which were treated with BCE4 showed less retention time (26.40±4.007) when compared to that of the disease induced animals (85.00±6.504). BCE3 (46.80±3.625), BCE2 (53.20±4.398) and BCE1 (62.00±3.421) didn't produce significant activity which was evidenced from the less alteration in retention time, as shown in FIG. 6. Decrease in retention time directly corresponds to the increase in memory. Based on the results from various studies at different dosage levels, it is evident that among all, BCE4 showed good anxiolytic property with significant increase in the memory. The anti-anxiety property can be achieved without compromising the memory potential.

Figure 7:
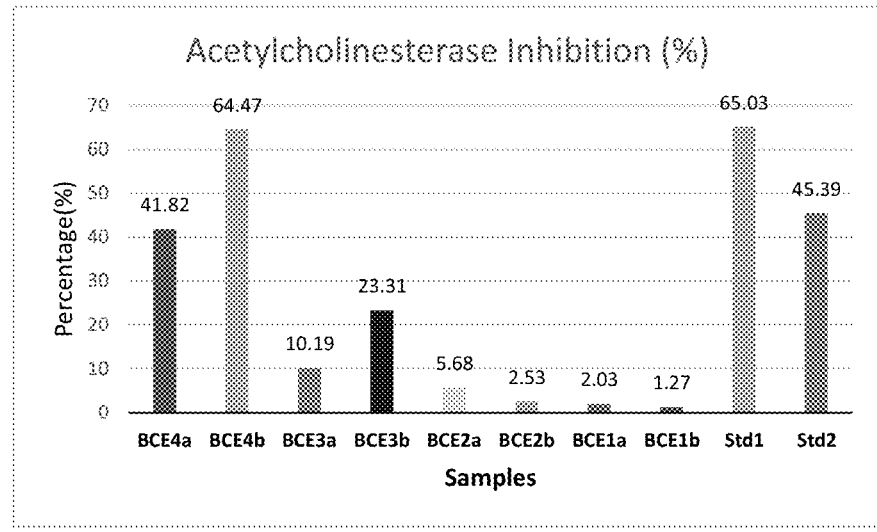
FIG. 7. shows effect of BCE compositions on AchE inhibitory assay using Ellman's method FIG. 8. shows effect of BCE compositions on activity on IMR-32 neuronal cell line.

III. In Vitro Studies to Prove the Mechanism of Action and Neurotransmitter Modulations Responsible for the Observed Anxiolytic Behaviour of Black Cumin Seed Extract Compositions with Significant Memory Enhancement During In Vivo Experiments:

Acetyl Cholinesterase Inhibitory Activity:

As discussed earlier catecholamines, especially Acetyl choline plays a vital role in memory functions. Acetylcholinesterase (AchE) is an enzyme that catalyses the breakdown of acetylcholine. So, the level of AchE inhibition is much necessary and is evaluated in-vitro by employing Elman's method. Donepezil a known AchE inhibitor is used as a standard drug. BCE4 at the dose of 10 µg produced 41.82% inhibition which is equal to that of donepezil (5 µg) with 45.39% inhibition. The same condition applies with BCE4 20 µg (64.47%) and donepezil 10 µg (65.03%). It is observed that BCE4 among the other extract compositions (BCE1, BCE2, BCE3) at both the doses increases the Acetyl choline level in brain which is evidenced by the Acetyl cholinesterase inhibitory activity, as shown in FIG. 7. Increase in AchE inhibitory activity shows the increase in Acetylcholine level, which in turn directly relates to increase in memory. In other words, black cumin extract composition containing not less than 5% TQ has the ability to inhibit AchE to provide better memory as compared to other compositions.

From the above experiment it is evident that BCE4 produced significant Acetylcholinesterase inhibitory activity when compared to that of BCE3, BCE2 and BCE1. Increase in AchE inhibitory activity shows the increase in Acetylcholine level, which in turn directly relates to increase in memory. In other words, black cumin composition containing not less than 5% TQ has the ability to inhibit AchE to provide better memory as compared to other compositions.

IV. Assessment of Anti-Anxiety Activity with Memory Enhancement Employing Cell-Based Assays to Demonstrate the Specified Activity of the Composition:

It is well known that anxiolytic agents when administered would impair memory. Anxiety and memory are two closely related paradigms. Elevated Acetyl Choline level in brain, specifically hippocampus will improve memory (Kalueff, *Neural Plasticity,* 2007. https://doi.org/10.1155/2007/78171). Memory and anxiety do not always follow synergetic "high anxiety-better memory" rule.

Memory and anxiety represent two overlapping CNS processes that closely interact at different levels. Both neuronal and glial cells along with brain mediators, neuropeptides and other key proteins co-operate in the regulation of memory and anxiety. Two different cell lines IMR-32 and U373-MG were used here in this study to evaluate the efficacy of the drug samples which contain three various concentrations of thymoquinone.

Study on IMR 32 (Neuronal Cell Line)

The IMR-32 cell line is a continuous hyperdiploid human neuroblastoma cell line and this cell line is proved to be an excellent source for the isolation of human neuronal nAChR subunit cDNAs. The acetyl choline neruotransmitters plays a vital role in both memory and behaviour. Furthermore, it is also stated that wild-type Human neuroblastoma IMR-32 cells have the ability to secrete long amyloid β-protein which acts as a neurotoxin when gets accumulated in brain (Groot Kormelink & Luyten, *FEBS Letters,* 1997; 400(3), 309-314).

Study on U373 MG (Glial Cell Line)

U373-MG cell line is a human astrocytoma cell lines. This cell line is proved to provoke inflammatory markers like IL-6 when triggered with certain inducers and it is also found that serotonin receptors can be expressed/unexpressed to modify the release of IL-6 (Lieb et al., *Journal of Neurochemistry,* 2005; 93(3), 549-559).

The black cumin extract composition rich in thymoquinone like BCE4, BCE3, BCE2 and normal cold pressed black seed extract (BCE1) were used. Adriamycin (ADR) is used as a positive control whereas Donepezil is used as a standard. All the drug samples were dissolved in DMSO for the SRB assay. The drug samples at the concentrations of 10 µg/ml, 20 µg/ml, 40 µg/ml, 80 µg/ml were used. The assay was done in triplicate and the average values were used to determine the percentage control growth.

A growth curve was constructed using percentage control growth versus drug concentration using the growth curve the concentration of drug causing 50% of cell death (LC50), concentration of drug causing total inhibition of cell growth (TGI) and finally the concentration of drug causing 50% inhibition of cell growth were calculated. GI 50 value of 10 or less than $10^{-6}$ is considered to demonstrate activity.

Figure 8:
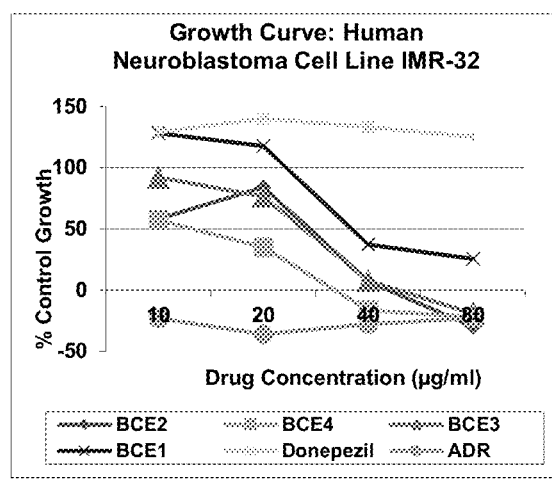

When evaluated on neuronal cell lines (IMR32), the GI 50 of BCE4 was found to be 4.3 which showed maximum activity among all the drug samples followed by other black cumin extracts which prove the activity dependence on the unique composition in black cumin oil rich in TQ. The standard used here Donepezil is found to have no activity whereas the positive control produced the GI 50 value of less than 10, as shown in FIG. 8. The above result confirms the action of BCE4 on neuronal cell lines containing Acetylcholine receptor subunits and are responsible for the improvement in memory as shown earlier by scopolamine induced animal model.

Figure 9:
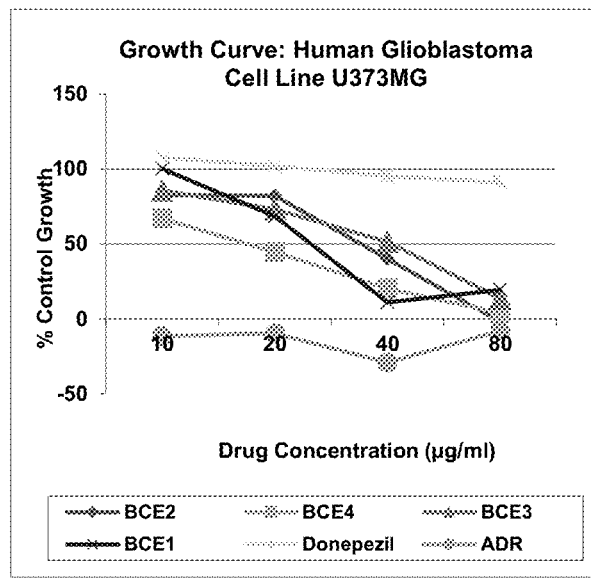
FIG. 9. shows effect of BCE compositions on activity on U373MG glial cell line.

When compared to neuroblastoma cell lines, the activity of black cumin oil on glial cells is found to produce less action. The GI 50 value of BCE4 was 18.3 whereas of BCE3, BCE2 and BCE1 were 43.3, 38.1 and 37.3 respectively. Here too Donepezil have not produced any significant activity whereas Adriamycin produced GI50 of less than 10. Action on glial cells shows the decrease in anxiety on BCE4 treated animals which are previously reported by ibotenic acid induced animal model, as shown in FIG. 9. From the above results, the black cumin oil composition with not less than 5% concentration of thymoquinone (BCE4) is found to be more effective and produced significant anxiolytic activity without affecting memory.

Example 10: Mechanism of Action of BCE4 in Anxiolytic Effect with Memory Enhancement To investigate the mechanism of action by which BCE4 acts, the expression of the glutamate neurotransmitter receptors, NR2A (NMDA receptors subtype) and gluR2 (AMPA receptor subtype) were examined against Ibotenic acid induced model. ChAT (cholinergic neuron marker in the hippocampus) expression was also examined against scopolamine induced model.

Figure 10:
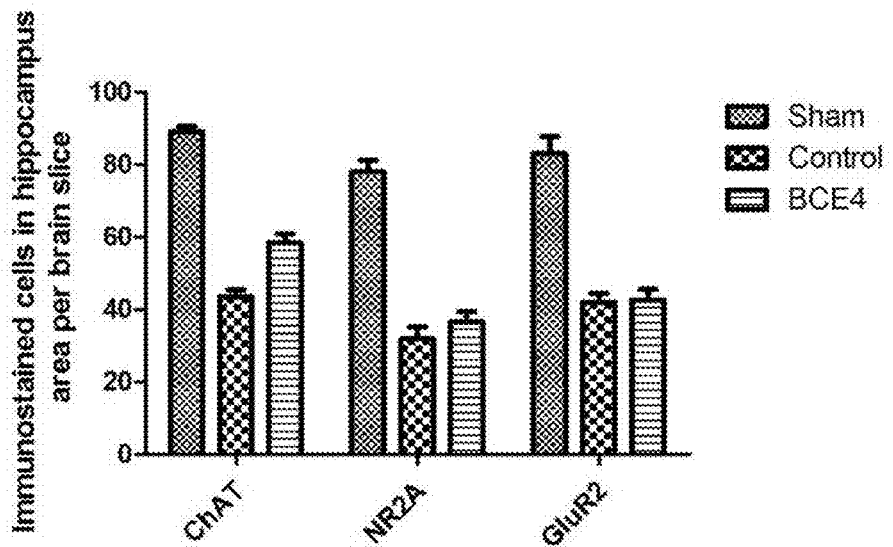
FIG. 10. shows expressions of genes to evaluate the mechanism of action of BCE.

BCE4 increased the survival of ChAT expressing neuronal cells in the hippocampus when compared to that of sham and control group which was evidenced by immunostained cells. In the immunostaining analysis of the glutamate receptor subtypes NR2A and GluR2, the expression was decreased in both subtypes when compared to that of sham group in the hippocampus. Thus, we can conclude that BCE4 may act by acting on glutamate receptors and cholinergic receptors and their subtypes which is responsible for its anxiolytic and memory improvement property. The results as shown in FIG. 10.

Example 11: Assessment of Toxicity

Thymoquinone rich composition of black cumin oil is used for the study. The toxicological studies on Albino Wistar rats showed that the BCE with 5% TQ is found to be non-toxic if administered at the dose range of 50 mg to 250 mg/kg orally, even if it is administered at daily dose continuously for several days. The non-toxicity is evidenced from our repeated dose 90 day's toxicity studies (subchronic toxicity) on Wistar rats of both sex. All the vital parameters were analysed at the end of the study and were found to be normal when compared to that of untreated rats.

Example 12: Effect of BCE4 Extract with 5% TQ on Sleep Quality Among Subjects with Sleep Disorders Sleep is an important component of mammalian homeostasis, vital for our survival. Sleep disorders are common in the general population and are associated with significant behavioural and health consequences. Insomnia, the most common sleep disorder, is associated with a 24 hour increase of ACTH and cortisol secretion, consistent with a disorder of central nervous system hyperarousal. Despite the prevalence of sleep complaints among psychiatric patients, few questionnaires have been specifically designed to measure sleep quality in clinical populations. Pittsburgh Sleep Quality Index (PSQI), Depression Anxiety Stress Scales-21 (DASS-21) and Hamilton Anxiety Rating Scale (HAM-A) were used in the study to evaluate improvement in sleep by the treatment with Black cumin oil containing 5% TQ (BCE4).

I. Pittsburgh Sleep Quality Index (PSQI)

Figure 11:
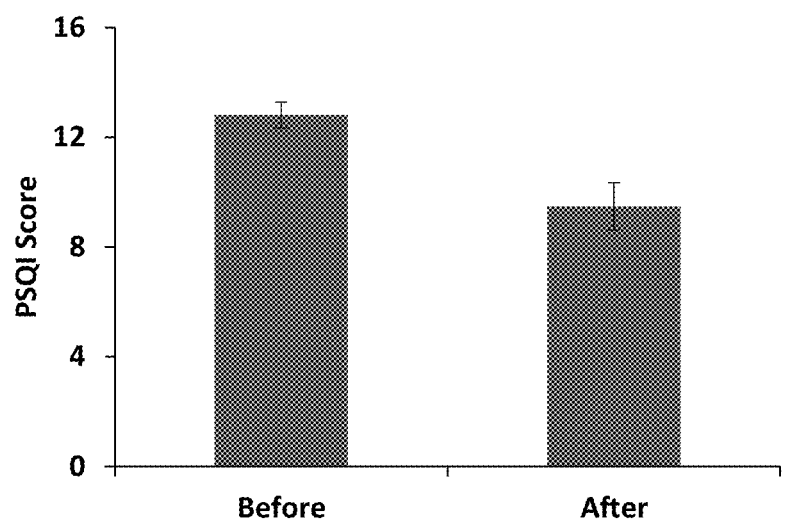
FIG. 11. shows effect of BCE compositions on Pittsburgh Sleep Quality Index (PSQI) before and after treatment with BCE4.

The Pittsburgh Sleep Quality Index (PSQI) is a self-rated questionnaire which assesses sleep quality and disturbances over a 1-month time interval. Nineteen individual items generate seven "component" scores: subjective sleep quality, sleep latency, sleep duration, habitual sleep efficiency, sleep disturbances, use of sleeping medication, and daytime dysfunction. Component scores range from 0 to 3 and are summed to obtain a global score, which ranges from 0 to 21. Higher scores suggest greater sleep disturbance; a global score more than 5 suggests a significant disturbance (Spira et al., *J Gerontol A Biol Sci Med Sci*. 2012; 67A (4): 433-439). PSQI is a well validated tool and it is been used in several sleep studies (Staples et al., *NPJ Schizophr.* 2017; 3(1):37). The results of our study showed a significant reduction after (30 Day) treatment with BCE4 (p≤0.001; from 12.81±0.47 to 9.48±0.86; 25.99%) when compared to baseline values. The results as shown in FIG. 11.

II. Depression Anxiety Stress Scales-21 (DASS-21)

Figure 12:
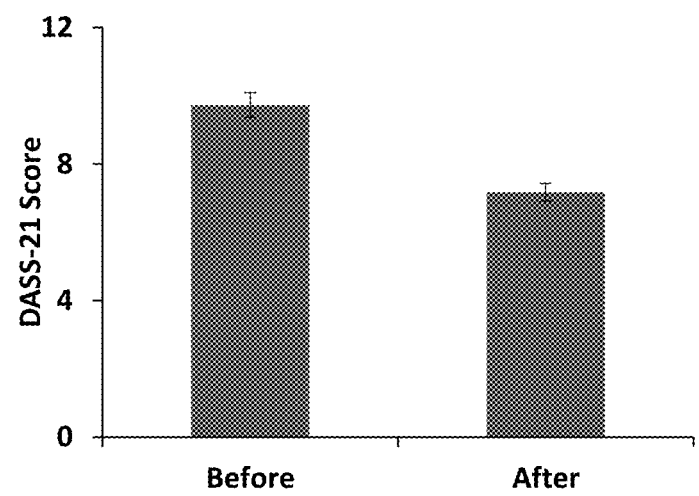
FIG. 12. shows effect of BCE compositions on Depression Anxiety Stress Scales-21 (DASS-21) before and after treatment with BCE4

The Depression Anxiety Stress Scales-21 (DASS-21) is a 21-item self-report questionnaire that is used extensively for measuring depression, anxiety, and stress in adults. The DASS-21 has three separate scales measuring depression, anxiety, and stress. Each scale has seven items. Respondents rate all items in terms of how often they experience them in the past week, using a 4-point scale, ranging from 0 (did not apply to me at all) to 3 (applied to me very much or most of the time). Sinclair et al., *Eval Health Prof.* 2012; 35(3):259-79, had conducted validation study of DASS-21. In our study the DASS-21 Score showed 26.31% reduction in comparison with baseline values (p≤0.001; from 9.73±0.36 to 7.17±0.26). The results as shown in FIG. 12.

Hamilton Anxiety Rating Scale (HAM-A)

Figure 13:
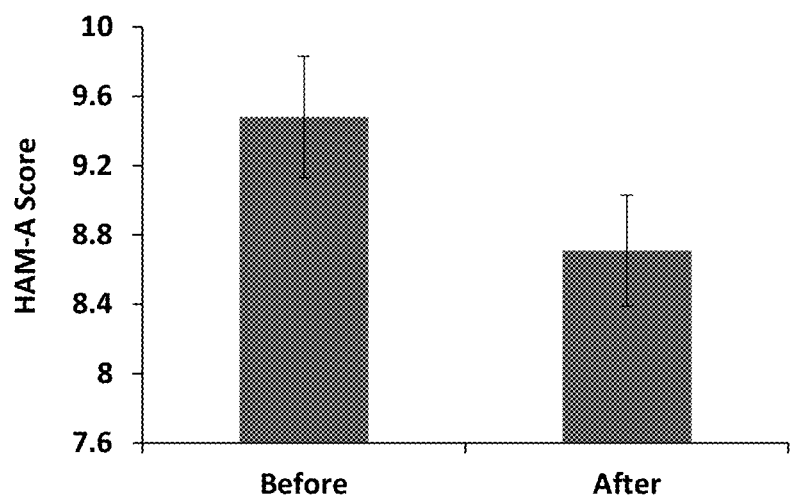
FIG. 13. shows effect of BCE compositions on Hamilton Anxiety Rating Scale (HAM-A) before and after treatment with BCE4

The Hamilton Anxiety Rating Scale (HAM-A) was one of the first rating scales developed to measure the severity of anxiety symptoms, and is still widely used today in both clinical and research settings (Dong et al., *Occupational Medicine*, 2017; 67:534-539). The scale consists of 14 items, each defined by a series of symptoms, and measures both psychic anxiety (mental agitation and psychological distress) and somatic anxiety (physical complaints related to anxiety). Each item is scored on a scale of 0 (not present) to 4 (severe), with a total score range of 0-56, where <17 indicates mild severity, 18-24 mild to moderate severity and 25-30 moderate to severe. The baseline values changed from 9.48±0.35 to 8.71±0.32 which was significantly different at p=0.083 (95% confidence level). The results as shown in FIG. 13.

Percentage Improvement in Component Scores

Figure 14:
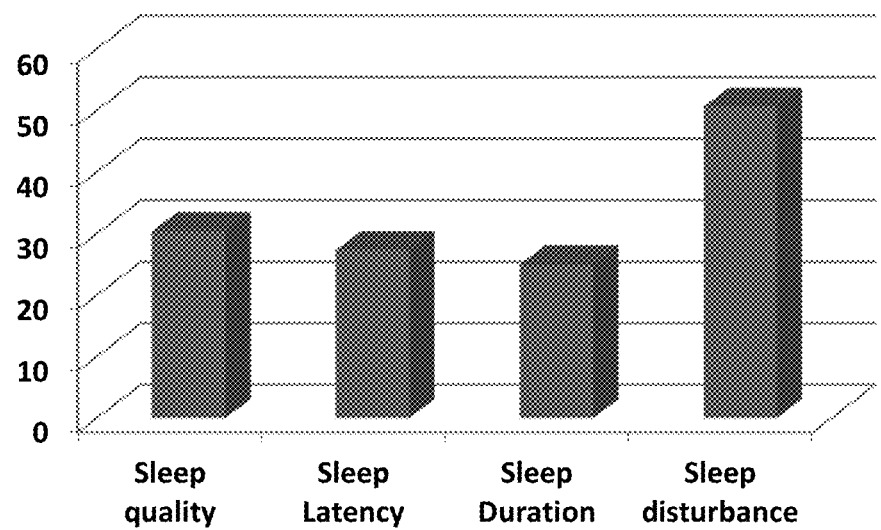
FIG. 14. shows effect of BCE compositions on percentage improvement in component scores of PSQI.

When we analysed the percentage improvement in component scores of PSQI; sleep quality showed 30.36%, sleep latency showed 27.32% reduction, sleep duration improved by 25% and sleep disturbances are reduced by 50.66% upon treatment with BCE4. The results as shown in FIG. 14.

What is claimed is:

1. A process for preparing a biologically active black cumin seed extract in free flowing powder form using black cumin seeds, comprising:
   (a) pre-treating powdered or flaked black cumin seeds with enzymes, followed by supercritical carbon dioxide extraction of the oil from the seeds to obtain a super critical extracted oil fraction which comprises non-volatile fixed oils rich in α-linoleic acid and volatile oils rich in thymoquinone;
   (b) extracting the residual black cumin seed material left after step (a) with a hydrophilic solvent to obtain residual black cumin seed extract;
   (c) spray-drying the residual black cumin seed extract from step (b) to obtain a residual black cumin seed free flowing powder;

(d) dissolving the residual black cumin seed extract free flowing powder from step (c) in water to obtain a residual black cumin seed extract solution at 10 to 25% total dissolved solids level;

(e) mixing the supercritical extracted oil fraction from step (a) with the residual black cumin seed solution obtained step (d), followed by homogenization or ultrasonication of the mixture thus obtained to produce an emulsion; and (f) spray-drying or freeze drying the emulsion from step (e) to obtain black cumin seed extracted oil composition in free flowing powder form;

wherein the black cumin seed extracted oil composition in free flowing powder form comprises thymoquinone in the range of 0.1 to 8%.

2. The process of claim 1, wherein the pre-treatment with at least one enzyme in step (a) is performed for 1 to 8 hours.

3. The process of claim 1, wherein the at least one enzyme is selected from the group consisting of: pectinase, amylase, galactosidase and protease.

4. The process of claim 1, wherein the supercritical extraction of black cumin seeds is performed using carbon dioxide at a pressure of from 100 to 220 bar and temperature of from 35 to 50° C.

5. The process of claim 1, wherein the hydrophilic solvent used for extraction in step (b) is water or a mixture of water and ethanol.

6. The process of claim 1, wherein step (b) of extracting the residual black cumin seed material using a hydrophilic solvent is done by solvent extraction in the temperature range of 50-60° C.

* * * * *